United States Patent [19]

Shirahata et al.

[11] Patent Number: 4,733,000

[45] Date of Patent: Mar. 22, 1988

[54] OPTICALLY ACTIVE 1-AMINO-2-(4-HYDROXYPHENYL)ETHYL-PHOSPHONIC ACID AND DERIVATIVES THEREOF

[75] Inventors: Kunikatsu Shirahata, Tokyo, Japan; Masaji Kasai, Rockville, Md.

[73] Assignee: Kyowa Hakko Kogyo Co., Ltd., Tokyo, Japan

[21] Appl. No.: 842,744

[22] Filed: Mar. 17, 1986

Related U.S. Application Data

[63] Continuation of Ser. No. 697,420, Feb. 1, 1985, abandoned, which is a continuation of Ser. No. 442,184, Nov. 16, 1982, abandoned.

[30] Foreign Application Priority Data

Nov. 17, 1981 [JP] Japan .................................. 56-184199

[51] Int. Cl.$^4$ ............................................... C07F 9/40
[52] U.S. Cl. ........................... 558/166; 260/502.5 D; 558/170
[58] Field of Search ......................... 558/170, 172, 166

[56] References Cited

U.S. PATENT DOCUMENTS

| 3,048,613 | 8/1962 | Ladd et al. ............................ 260/944 |
| 4,016,148 | 4/1977 | Atherton et al. ............ 260/112.5 R |
| 4,100,275 | 7/1978 | Atherton et al. .................... 424/211 |
| 4,127,649 | 11/1978 | Atherton et al. .................... 424/177 |
| 4,134,972 | 1/1979 | Atherton et al. .................... 424/177 |
| 4,213,969 | 7/1980 | Baylis .................................. 424/177 |
| 4,250,085 | 2/1981 | Atherton et al. ............ 260/112.5 R |

FOREIGN PATENT DOCUMENTS 61172  9/1982  European Pat. Off. .

OTHER PUBLICATIONS

Iron et al, "Chem. Absts.", vol. 95, (1981) 181689m.
Sofer: Biochemical Regulation of Blood Pressure 165:205 (1981).
Pharm. Soc. of Japan: 7th Symposium on Medicinal Chemistry 21:4 (1985).

*Primary Examiner*—Anton H. Sutto
*Attorney, Agent, or Firm*—Fitzpatrick, Cella, Harper & Scinto

[57] ABSTRACT

Disclosure is optically active 1-amino-2-(hydroxyphenyl) ethylphosphonic acid and derivatives thereof which are useful as intermediates for the preparation of phosphorus-containing oligopeptides exhibiting hypotensive activity.

4 Claims, No Drawings

OPTICALLY ACTIVE 1-AMINO-2-(4-HYDROXYPHENYL)ETHYLPHOSPHONIC ACID AND DERIVATIVES THEREOF

This application is a continuation of application Ser. No. 697,420 filed Feb. 1, 1985, now abandoned, which is a continuation of application Ser. No. 442,184, filed Nov. 16, 1982, now abandoned.

RELATED APPLICATIONS

The present invention is related generally to the invention disclosed in U.S. patent application Ser. No. 912,685, filed Sept. 26, 1986, now U.S. Pat. No. 4,683,220, for Novel Physiologically Active Substance K-26, A Process for Production Thereof and A Pharmaceutical Composition Containing the Same, and U.S patent application Ser. No. 407,082 filed Aug. 11, 1982, now U.S. Pat. No. 4,522,812, issued June 11, 1985, for Novel Physiologically active substance K-4, A Process for Preparation Thereof and a Pharmaceutical Composition Containing the Same.

BACKGROUND OF THE INVENTION

The present invention pertains to optically active 1-amino-2-(4-hydroxyphenyl) ethylphosphonic acid and its derivatives thereof. The compounds of the present invention are useful as intermediates for the synthesis of phosphorus-containing oligopeptides having hypotensive activity such as those compounds disclosed in the aforementioned, commonly owned, related applications. 1-amino-2-(4-hydroxyphenyl) ethylphosphonic acid in racemic form is a known compound and is described in Chemical Abstracts 62, 6510e (1965). In addition, Austrian Pat. No. 342,192 discloses compounds represented by the formula:

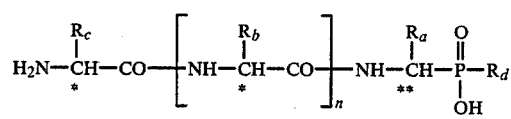

wherein $R_a$ is hydrogen, lower alkyl, lower cycloalkyl, lower cycloalkyl-lower alkyl, aryl or aryl-lower alkyl where these residual groups may be substituted by one or more of amino, hydroxy, thio, methylthio, carboxyl or guanidino; $R_b$ and $R_c$ are residual groups of α-amino acid; $R_d$ is hydroxyl or methyl; and n is 0,1,2 or 3. The carbons indicated by one asterisk have L-configuration, and the carbon indicated by two asterisks has R configuration; and according to the patent, the compounds are useful for increasing the antibacterial activity of cephalosporin or penicillin antibiotics, etc.

DESCRIPTION OF THE INVENTION

In accordance with the the present invention, there is provided novel compounds represented by formula (X):

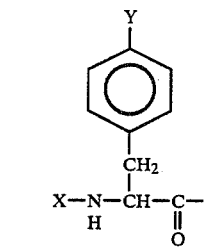

wherein R is hydrogen, lower alkyl, or substituted or unsubstituted phenylalkyl; $R_1$ is hydrogen or a group represented by:

$$\begin{array}{c} Y \\ | \\ \bigcirc \\ | \\ CH_2 \\ | \\ X-N-CH-C- \\ H \quad \quad \| \\ \quad \quad \quad O \end{array}$$

wherein X is hydrogen, or an amino-protecting group usually used in peptide synthesis; Y is hydrogen, hydroxyl or a group represented by $OY_1$ (wherein $Y_1$ is a hydroxyl-protecting group usually used in peptide synthesis); Z is hydrogen or a group represented by $Y_1$ (wherein $Y_1$ has the same definition as above); the aromatic amino acid part has L-configuration, and the 1-amino-2-(4-hydroxyphenyl) ethylphosphonic acid part has negative specific rotation.

The term "lower alkyl" in the definition of R means straight or branched alkyl having 1–6 carbon atoms. The term "alkyl" in "substituted or unsubstituted phenylalkyl" in the definition of R means straight or branched alkyl having 1–6 carbon atoms, and the substitutent includes halo such as chloro and bromo, nitro, alkoxy having 1–3 carbon atoms such as methoxy and ethoxy, etc. Halo or alkoxy substituted at the p-position is especially preferable as the substituent. The amino-protecting group usually used in peptide synthesis in the definition of X includes benzyloxycarbonyl, t-butoxycarbonyl and the like. The hydroxyl-protecting group usually used in peptide synthesis in the definition of $Y_1$ includes alkyl such as methyl and ethyl, arylalkyl such as benzyl, benzyloxycarbonyl, and the like.

Among those compounds represented by formula (X), the compounds represented by the following formulae (I) and (II) are typical examples of the compounds of the present invention:

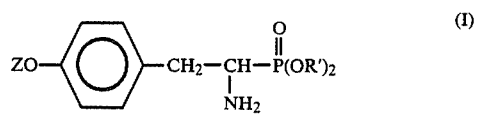

wherein R' is hydrogen or lower alkyl and Z has the same definition as above;

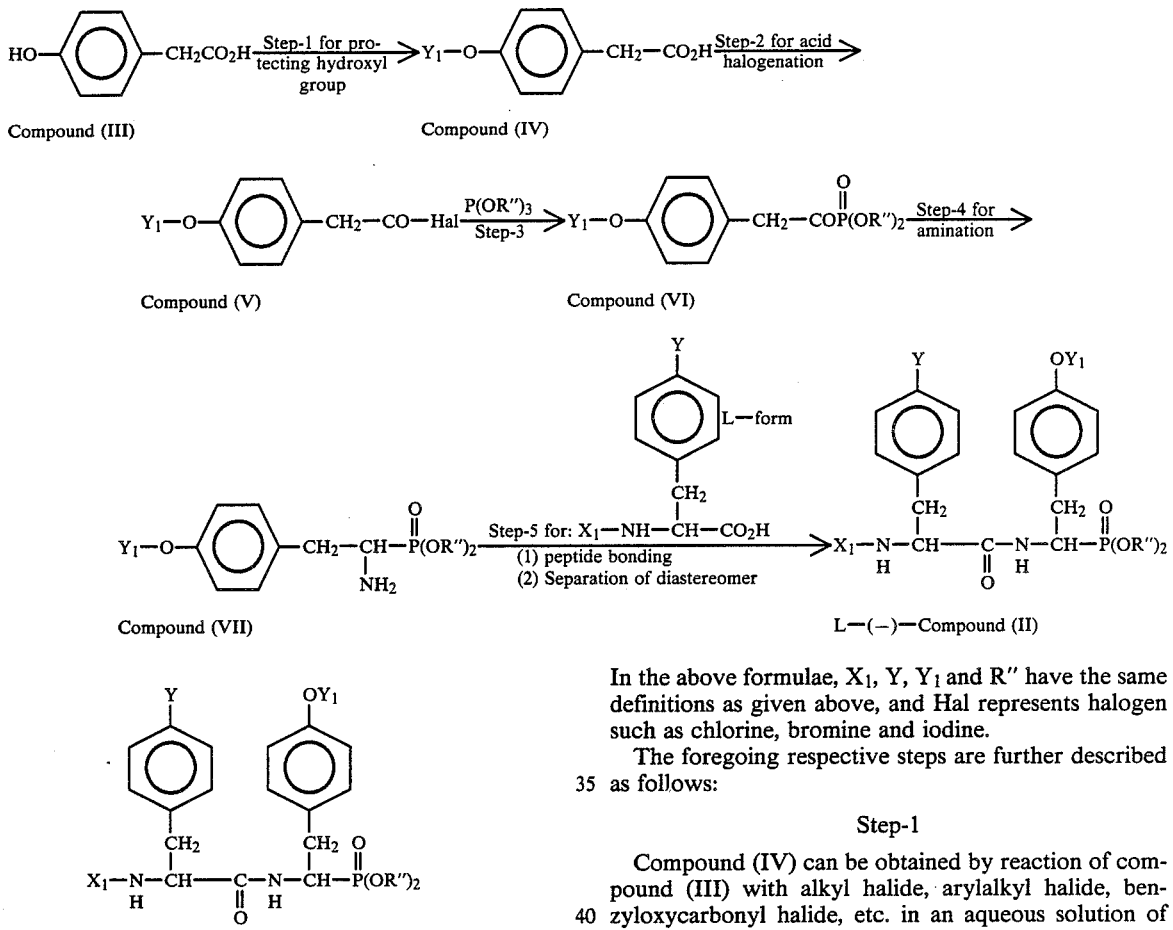

wherein R″ is lower alkyl, or substituted or unsubstituted phenylalkyl; X₁ is an amino-protecting group usually used in peptide synthesis; and Y and Y₁ have the same definition as above. The compounds represented by the formulae (I), (II), . . . are sometimes hereinafter referred to as "Compound (I), Compound (II), . . . ", respectively.

The present compounds are useful as an intermediate for the synthesis of phosphorus-containing oligopeptides having useful physiological activity, for example, hypotensive activity. The phosphorus-containing oligopeptides include N-(N-acetyl-L-isoleucyl-L-tyrosyl)-(−)-1-amino-2-(4-hydroxyphenyl) ethylphosphonic acid and N-(N-methyl-L-valyl-L-phenylalanyl)-(−)-1-amino-2-(4-hydroxyphenyl) ethylphosphonic acid, etc.

Such phosphorus-containing oligopeptides can be readily produced from Compound (II) where the aromatic amino acid part has L-configuration and the 1-amino-2-(4-hydroxyphenyl) ethylphosphonic acid part has negative specific rotation (hereinafter referred to as L-(−)-Compound (II)) as a starting compound without using any optical resolution means. Moreover, the starting compound can be produced from Compound (I) where the 1-amino-2-(4-hydroxyphenyl) ethylphosphonic acid part has negative specific rotation (hereinafter referred to as (−)-Compound (I)), or an optically inactive Compound (I) (racemic compound).

The compounds of the present invention may be prepared by the following reaction steps.

In the above formulae, $X_1$, $Y$, $Y_1$ and R″ have the same definitions as given above, and Hal represents halogen such as chlorine, bromine and iodine.

The foregoing respective steps are further described as follows:

Step-1

Compound (IV) can be obtained by reaction of compound (III) with alkyl halide, arylalkyl halide, benzyloxycarbonyl halide, etc. in an aqueous solution of potassium hydroxide, sodium hydroxide, alkali carbonate, or the like. As the alkyl halide, methyl iodide, ethyl iodide, etc. and as the arylalkyl halide, benzyl bromide, benzyl chloride, etc. are used. The reaction is carried out at room temperature for 2–24 hours.

Step-2

Compound (V) can be obtained from compound (IV) by a method for deriving an acid halide from carboxylic acid, usually used in organic synthesis. For example, compound (IV) is dissolved in thionyl chloride, and boiled for 1–12 hours, whereby compound (V) is obtained.

Step-3

Compound (VI) can be obtained by reacting Compound (V) with phosphite ester represented by the formula P(OR″)₃ wherein R″ has the same meaning as defined above in an inert solvent with stirring at room temperature or at an elevated temperature for 30 minutes to 3 days, preferably in a nitrogen gas stream.

Step-4

Compound (VII) can be obtained from compound (VI) by a method for converting a ketone to an amino group, usually used in organic synthesis. For example, compound (VI) is reacted with hydroxylamine or dialkyl-hydrazine at 10°–60° C. for 0.5–12 hours to derive the corresponding oxime or dialkylhydrazone, which is subjected to catalytic reduction using a catalyst, or to reduction reaction using a reducing agent such as aluminium amalgam or zinc-acetic acid (0°–100° C. for 1–24 hours), whereby compound (VII) is obtained.

Step-5

Compound (II) can be obtained by reacting Compound (VII) with an amino acid derivative in L-form represented by the formula:

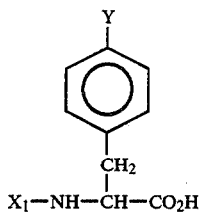

wherein $X_1$ and Y have the same definition as the presence of a condensing agent usually used in peptide synthesis in an inert solvent at $-20°$ C. to room temperature for a few hours to 3 days, and successively by separating and purifying the reaction product according to methods usually used in organic synthesis. Alternatively, the amino acid derivative is converted to an active ester derivative usually used in peptide synthesis or an acid anhydride thereof, and then the latter derivative is condensed with compound (VII), and thereafter compound (II) can be obtained by separation.

As the condensing agent, N,N'-dicyclohexylcarbodiimide (hereinafter referred to as "DCC"), DCC and N-hydroxysuccinimide, DDC and 1-oxybenzotriazole, etc. can be used. The inert solvent is a solvent usually used in peptide synthesis, and includes an ether such as tetrahydrofuran and ethylene glycol dimethyl ether, an amide such as N,N-dimethylformamide, and an halogenated hydrocarbon such as methylene chloride, alone or in combination. As the active ester, a substituted phenyl ester such as p-nitrophenyl ester, and a dicarboxylic acid imide ester such as N-hydroxysuccinimide ester can be used.

Step-6

Production of (−)-Compound (I)

L-(−)-Compound (II) or a compound obtained by eliminating the protective group $Y_1$ of L-(−)-Compound (II) according to a conventional elimination method is hydrolyzed under such conditions that the asymmetry of 1-amino-2-(4-hydroxyphenyl) ethylphosphonic acid is maintained to produce (−)-1-amino-2-(4-substituted or unsubstituted hydroxyphenyl) ethylphosphonic acid represented by the planar formula [Ia]:

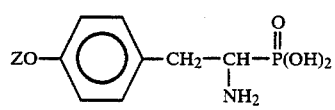

wherein Z has the same meaning as defined above. The hydrolysis can be carried out by heating L-(−)-Compound (II) in an aqueous solution of mineral acid such as hydrochloric acid at 100°–120° C. for half a day to two days. Then, the reaction mixture is subjected to separation and purification by methods used in ordinary organic synthesis to obtain (−)-Compound [Ia].

(−)-Compound [Ia] is either treated with etherial diazomethane at room temperature for 5 minutes to 3 hours, or reacted with a lower alkanol such as methanol, ethanol, propanol and butanol in the presence of DCC in a mixed solvent of dimethylformamide and pyridine (2:1) at room temperature overnight to produce an ester represented by the formula [Ib].

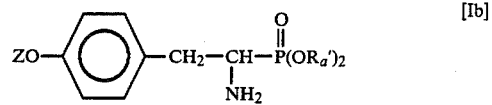

wherein $R_a'$ is lower alkyl and Z has the same meaning as defined above. (−)-Compound [Ib] can also be obtained according to a method illustrated in Example 7.

(−)-Compound (I) consists of (−)-Compound [Ia] and (−)-Compound [Ib].

L-(−)-Compound (II) can be obtained by conducting the reaction of Step-5 using (−)-Compound (I) in place of Compound (VII).

Certain specific embodiments of the invention are illustrated by the following representative examples.

EXAMPLE 1

(Step-1)

In this example, 1.52 grams of 4-hydroxyphenylacetic acid and 1.2 g of caustic soda are dissolved in 30 ml of water-ethanol (2:1), admixed with 2.97 ml of benzyl bromide, and stirred at room temperature for one day. The reaction solution is adjusted to pH 2 with hydrochloric acid, and extracted with ethyl acetate. The extract is washed with water and dried over anhydrous sodium sulfate. The solvent is distilled off under reduced pressure, and the residue, is recrystallized from benzene-n-hexane, whereby 1.71 g of the desired compound is obtained as colorless crystals having the following physical properties (yield: 71%).

Melting point: 123°–124° C.

$^1$H-NMR spectrum (CDCl$_3$)δ: 3.56(s, 2H), 5.02(s, 2H), 6.87(d, 2H), 7.17(d, 2H), 7.33(s, 5H), 10.7(bs, 1H)

IR(KBr): 3040, 1685, 1507, 1240 cm$^{-1}$

From the above analysis, the substance is identified as 4-benzyloxyphenylacetic acid.

EXAMPLE 2

(Steps-2, 3, 4)

In this example, 6.05 g of 4-benzyloxyphenylacetic acid obtained as in Example 1, is dissolved in 125 ml of thionyl chloride, and boiled for 4 hours. Excess thionyl chloride is distilled off under reduced pressure, and the residue is dried, whereby 4-benzyloxyphenylacetic acid chloride is obtained. The thus obtained product is then dissolved in 25 ml of anhydrous benzene, and the resulting solution is added dropwise to 8.3 g of triethyl phosphite in a nitrogen gas stream with stirring under ice cooling.

Thirty minutes thereafter, the temperature is elevated to room temperature, and the solution is stirred for one day, whereby diethyl 4-benzyloxyphenylacetylphosphonate is obtained. The substance is unstable and thus is admixed with 50 ml of ethanol and 3 ml of anhydrous pyridine without purification with stirring. Then, the mixture is admixed with 1.92 g of hydroxylamine hydrochloride and stirred at room temperature for 4 hours. The reaction solution is admixed with 200 ml of water and 15 ml of 2N HCl, and extracted with chloroform. The organic layer is washed with water and then dried. The solvent is distilled off under reduced pressure, and the residue is subjected to silica gel column chromatography (chloroform:acetone=9:1), whereby 5.4 g of the desired product is obtained as a light yellow oily substance having the following physical properties (yield: 57%).

Mass spectrum of the substance shows a molecular ion peak at m/Z 377.

$^1$H-NMR spectrum (CDCl$_3$): main peaks are δ: 1.19(t, 6H), 3.7 - 4.2(m, 6H), 5.02(s, 2H), 6.86(d, 2H), 7.26 (d, 2H), 7.36(bs, 5H)

From the above analysis, the substance is identified as diethyl 4-benzyloxyphenylacetylphosphonate oxime.

Then, 860 mg of diethyl 4-benzyloxyphenylacetylphosphonate oxime is dissolved in 4.6 ml of formic acid, admixed with 600 mg of zinc dust with stirring under ice cooling, and stirred for 3 hours. The reaction solution is filtered, and the filtrate is admixed with 50 ml of ethyl acetate. The organic layer is washed with a saturated aqueous sodium bicarbonate solution and then with water, and dried over anhydrous sodium sulfate. The solvent is distilled off under reduced pressure, and the residue is subjected to silica gel column chromatography (chloroform:methanol=98:2), whereby 540 mg of the desired compound is obtained as a colorless solid having the following physical properties (yield: 65%).

Melting point: 53°-55° C.

| Elemental analysis | C | H | N |
| --- | --- | --- | --- |
| Found | 62.6 | 6.7 | 3.6% |
| Calculated (as C$_{19}$H$_{26}$NO$_4$P) | 62.8 | 7.2 | 3.9% |

Mass spectrum of the substance shows a molecular ion peak at m/Z 363.

$^1$H-NMR(CDCl$_3$): main peaks are δ: 1.33(t, 6H), 2.98(m, 1H), 3.17(m, 2H), 4.16(m, 4H), 5.03(s, 2H), 6.91(d, 2H), 7.15(d, 2H), 7.35(bs, 5H)

IR(CHCl$_3$) 1505, 1230, 1046, 1020 cm$^{-1}$

From the above analysis, the substance is identified as diethyl 1-amino-2-(4-benzyloxyphenyl) ethylphosphonate.

EXAMPLE 3

(Step-5)

In this example, 138 mg of diethyl 1-amino-2-(4-benzyloxyphenyl) ethylphosphonate, 142 mg of N-t-butoxycarbonyl-O-benzyl-L-tyrosine, and 44 mg of N-hydroxysuccinimide are dissolved in 4 ml of anhydrous ethylene glycol dimethyl ether, and stirred on a sodium chloride-ice bath. The solution is admixed with 86 mg of DCC and stirred under cooling for 2 hours, and, thereafter, at room temperature for 26 hours. The formed N,N'-dicyclohexylurea is filtered off, and the filtrate is admixed with 100 ml of ethyl acetate, washed with water, and then dried over anhydrous sodium sulfate. The solvent is distilled off under reduced pressure, and then the residue is subjected to silica gel thin layer chromatography for fractionation recovery, developed with a mixed solvent of chloroform:acetone=9:1, and separated into the portion of Rf=0.39 and the portion of Rf=0.27. The portion of Rf=0.39 is collected, and eluted with the same solvent. The solvent is distilled off under reduced pressure, whereby 100 mg of the desired compound is obtained as a colorless glass-like substance having the following physical properties (yield: 73%).

$[\alpha]_D^{26}$ = −40.2° (c 0.92, MeOH)

IR(CHCl$_3$): 1673, 1504, 1234, 1042, 1018 cm$^{-1}$ $^1$H-NMR(CDCl$_3$) main peaks are δ: 1.23(t, 3H), 1.28 (t, 3H), 1.38(s, 9H), 2.5–4.8(m, 10H), 4.99(s, 2H), 5.01(s, 2H), 6.8–7.1(m, 8H), 7.36(bs, 10H)

Mass spectrum of the substance shows a molecular ion peak at m/Z 716.

From the above analysis, the substance is identified as diethyl N-(N-t-butoxycarbonyl-O-benzyl-L-tyrosyl)-(−)-1-amino-2-(4-benzyloxyphenyl) ethylphosphonate.

EXAMPLE 4

(Step-5)

In this example, 408 mg of diethyl 1-amino-2-(4-benzyloxyphenyl) ethylphosphonate, 336 mg of N-benzyloxycarbonyl-L-phenylalanine, and 129 mg of N-hydroxysuccinimide are dissolved in 11 ml of anhydrous ethylene glycol dimethyl ether, and the solution is stirred on a sodium chlorideice bath. The solution is admixed with 255 mg of DCC and stirred for 2.5 hours. Then, the solution is left standing in a refrigerator (about 5° C.) for 2.5 days. The formed N,N'-dicyclohexylurea is filtered off, and the filtrate is admixed with 150 ml of ethyl acetate. After treating the filtrate in the same manner as that of Example 3, the residue is subjected to silica gel column chromatography (chloroform:acetone=9:1; separated into the portion of Rf=0.33 and the portion of Rf=0.25 by silica gel thin layer chromatography with the same solvent), whereby 265 mg of the desired compound of Rf 0.33 is obtained as a colorless glass-like substance having the following physical properties (yield: 73%).

$[\alpha]_D^{26}$ = −48.5° (c 1.14, MeOH)

IR(CHCl$_3$): 1715, 1677, 1507, 1231, 1043, 1020 cm$^{-1}$ $^1$H-NMR(CDCl$_3$) main peaks are δ: 1.20(t, 3H), 1.27 (t, 3H), 2.6–5.0(m, 10H), 4.95(s, 2H), 5.01(s, 2H), 6.82(d, 2H), 7.08(d, 2H), 7.1–7.3(15H)

Mass spectrum of the substance shows a molecular ion peak at m/Z 644.

From the above analysis, the substance is identified as diethyl N-(N-benzyloxycarbonyl-L-phenylalanyl)-(−)-1-amino-2-(4-benzyloxyphenyl) ethylphosphonate.

EXAMPLE 5

(Step-6)

In this example, 93 mg of diethyl N-(N-t-butoxycarbonyl-O-benzyl-L-tyrosyl)-(−)-1-amino-2-(4-benzyloxyphenyl) ethylphosphonate is added to 26 ml of 6N hydrochloric acid, and heated at 110° C. in a sealed tube for 20 hours. After removing the seal, water is added, and the mixture is evaporated to dryness under reduced pressure. This operation is repeated three times, and then the the residue is subjected to silica gel column chromatography (i-propanol:chloroform:concentrated aqua ammonia= 3:1:2), whereby the desired compound is obtained. The compound is dissolved in a small amount of an aqueous 0.2N caustic soda solution, and the solution is passed through a column of Amberlite CG-50 (H$^+$type), followed by elution with water. After freeze-drying, 22 mg of the desired compound is obtained as a light brown solid having the following physical properties (yield: 80%).

Melting point: 300° C. or higher $[\alpha]_D^{26} = -40° \pm 2°$ (c 0.51, 1.0N - NaOH)

IR(KBr): 3420, 3240, 1610, 1511, 1248, 1146, 1022 cm$^{-1}$ $^1$H-NMR(D$_2$O, pD 7.6) δ: 2.8(m, 1H), 3.39(m, 2H), 6.97(d, 2H), 7.32(d, 2H)

13C-NMR(D$_2$O, pD 7.6) δ: 35.0, 53.5(d), 116.7, 129.7(d) 131.3, 155.5

From the above analysis, the substance is identified as (—)-1-amino-2-(4-hydroxyphenyl) ethylphosphonic acid.

EXAMPLE 6

(Step-6)

In this example, 78 mg of diethyl N-(N-benzyloxycarbonyl-L-phenylalanyl,-(—)-1-amino-2-(4-benzyloxyphenyl) ethylphosphonate is added to 24 ml of 6N hydrochloric acid. After following the procedure of Example 5, 16 mg of the desired compound is obtained (yield: 61%). The substance is identical with the compound in Example 5 in thin layer chromatography, $^1$H-NMR, IR, specific rotation, etc., and thus is identified as (—)-1-amino-2-(4-hydroxyphenyl) ethylphosphonic acid.

EXAMPLE 7

In this example, the following reaction steps are carried out:

an aqueous 1N sodium hydroxide solution, and admixed with 3 ml of ethanol. Then, the solution is admixed with 55 μl of benzyl bromide, and stirred at room temperature for one day. The reaction solution is adjusted to pH 2 with hydrochloric acid, and extracted with ethyl acetate. The extract is washed with water, and dried over anhydrous sodium sulfate. Then, the solvent is distilled off under reduced pressure whereby 80 mg of the desired compound is obtained.

In the second step, the 80 mg of the thus obtained crude (—)-1-amino-2-(4-benzyloxyphenyl) ethylphosphonic acid is dissolved in 5 ml of nitromethane, and admixed with 200 μl of triethyl phosphite, and the mixture is heated to 100° C. for 12 hours with stirring. The reaction solution is then admixed with ethyl acetate, and the organic layer is washed with an aqueous saturated sodium bicarbonate solution, and then with water, and dried over anhydrous sodium sulfate. The solvent is distilled off under reduced pressure, and the residue is subjected to silica gel column chromatography (chloroform:methanol=98:2), whereby 74 mg of the desired compound is obtained as a colorless solid (yield: 78%).

The 74 mg of the thus obtained diethyl (—)-1-amino-2-(4-benzyloxyphenyl) ethylphosphonate, 76 mg of N-t-butoxycarbonyl-O-benzyl-L-tyrosine, and 24 mg of N-hydroxysuccinimide are dissolved in 3 ml of anhydrous ethylene glycol dimethyl ether, and the solution is

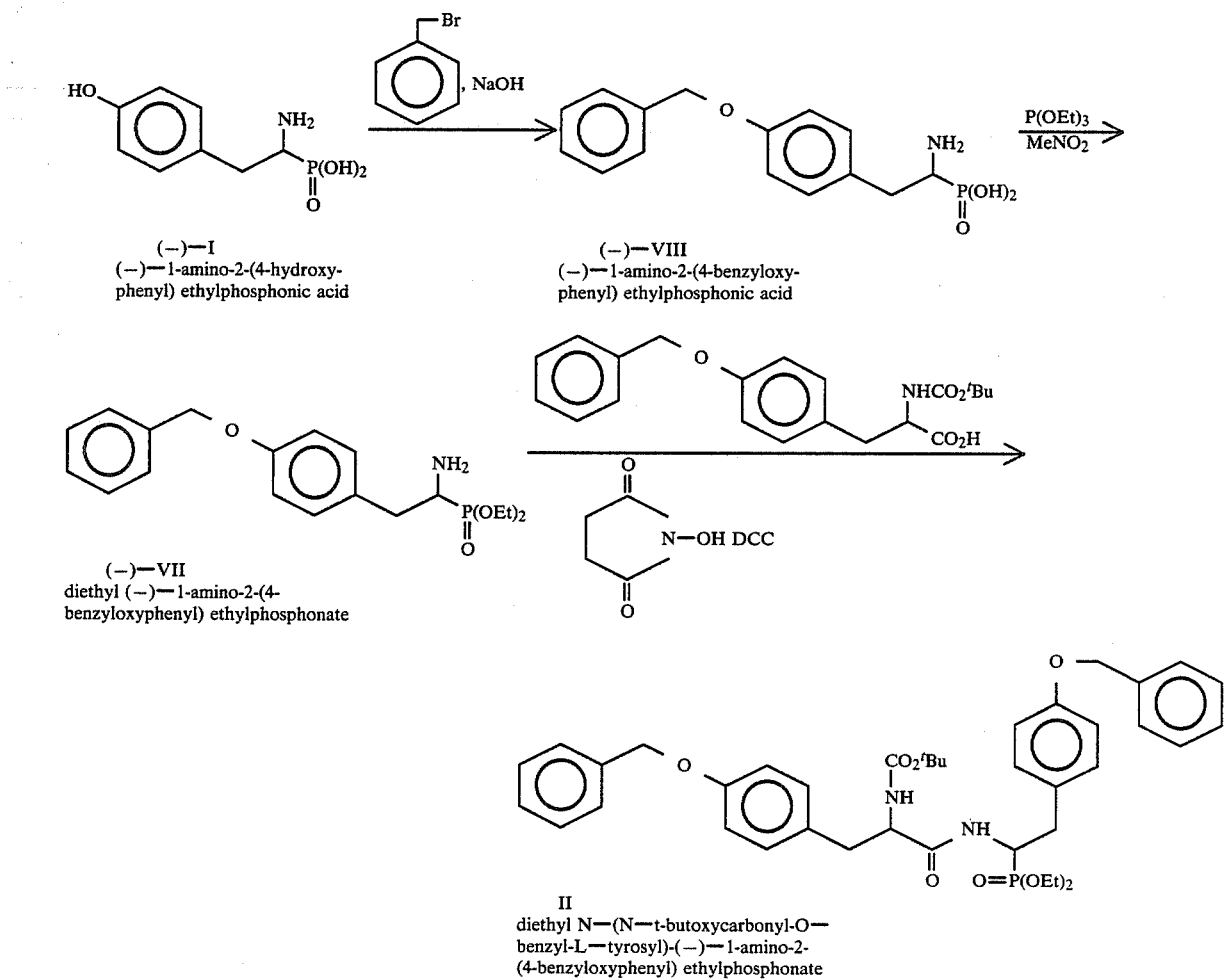

In the first step, 83 mg of (—)-1-amino-2-(4-hydroxyphenyl) ethylphosphonic acid is dissolved in 1.5 ml of stirred on a sodium chloride-ice bath. Then, the solution is admixed with 46 mg of DCC, stirred under cooling for 2 hours, and thereafter at room temperature for 26 hours. The formed N,N'-dicyclohexylurea is filtered off, and the filtrate is admixed with 50 ml of ethyl acetate, washed with water, and then dried over anhydrous sodium sulfate. The solvent is distilled off under reduced pressure, and then the residue is purified by silica gel thin layer chromatography for fractionation recovery (developing solvent: chloroform: acetone=9:1), whereby 101 mg of the desired compound is obtained as a colorless glass-like substance (yield: 69%).

The properties of the thus obtained compound are identical with those of diethyl N-(N-t-butoxycarbonyl-O-benzyl-L-tyrosyl)-(−)-1-amino-2-(4-benzyloxyphenyl) ethylphosphonate obtained in Example 3.

The synthesis of phosphorus-containing oligopeptides having physiological activity from the compounds obtained according to the present invention is illustrated by the following Reference Examples.

Reference Example 1

In this example, 41 mg of diethyl N-(N-t-butoxycarbonyl-O-benzyl-L-tyrosyl)-(−)-1-amino-2-(4-benzyloxyphenyl) ethylphosphonate (see Example 3) is dissolved in 4 ml of ethyl acetate, admixed with 1 ml of 10% hydrochloric acid-methanol solution, and stirred at room temperature for one day. Then, the solution is admixed with 50 ml of ethyl acetate, washed with aqueous sodium bicarbonate, and then with water, and dried over anhydrous sodium sulfate. The solution is subjected to silica gel thin layer chromatography for fractionation recovery (chloroform: methanol=95:5), whereby 26 mg of a colorless, glass-like substance is obtained having the following physical properties (yield: 73%).

$[\alpha]_D^{26} = -40.4°$ (c 0.92, MeOH)
IR(CHCl$_3$): 3340, 1679, 1505, 1231, 1044, 1019 cm$^{-1}$
Mass spectrum of the substance shows a molecular ion peak at m/Z 616.

The substance is thus identified as diethyl N-(O-benzyl-L-tyrosyl)-(−)-1-amino-2-(4-benzyloxyphenyl) ethylphosphonate.

REFERENCE EXAMPLE 2

In this example, 75 mg of diethyl N-(N-benzyloxycarbonyl-L-phenylalanyl)-(−)-1-amino-2-(4-benzyloxyphenyl) ethylphosphonate (see Example 4) is dissolved in 5 ml of methanol-acetic acid (4:1), admixed with 40 mg of 10% palladium-carbon, and subjected to catalytic reduction for 8 hours. The catalyst is filtered off, and the filtrate is distilled off under reduced pressure. The residue is then subjected to silica gel thin layer chromatography for fractionation recovery (chloroform:methanol=9:1), whereby 40 mg of the desired compound is obtained as a colorless glass-like substance having the following physical properties (yield: 83%).

$[\alpha]_D^{26} = -63.0°$ (c 1.36, MeOH)
IR(CHCl$_3$): 3320, 1660, 1508, 1226, 1041, 1020 cm$^{-1}$
$^1$H-NMR(CD$_3$OD): main peaks are δ: 1.29(m, 6H), 2.5–3.7(m, 5H), 4.1(m, 4H), 4.56(m, 1H), 6.70(d, 2H), 7.05(d, 2H), 7.2(5H)
Mass spectrum of the substance shows a molecular ion peak at m/Z 420.

The substance is thus identified as diethyl N-(L-phenylalanyl)-(−)-1-amino-2-(4-hydroxyphenyl) ethylphosphonate.

REFERENCE EXAMPLE 3

In this example, 26 mg of the compound obtained in Reference Example 1, 7 mg of N-acetyl-L-isoleucine, and 5 mg of N-hydroxysuccinimide are dissolved in 1 ml of anhydrous ethylene glycol dimethyl ether, and the solution is stirred on a sodium chloride-ice bath. Then, the solution is admixed with 9 mg of DCC with stirring, allowed to stand to raise the temperature to room temperature and, thereafter, reacted for 26 hours. The formed N,N'-dicyclohexylurea is removed, and the solvent is distilled off under reduced pressure. The residue is subjected to silica gel thin layer chromatography for fractionation recovery (chloroform:methanol=97:3), whereby 15 mg of the desired compound is obtained as a white solid having the following physical properties (yield: 46%).

Melting point: 145°–147° C.
$[\alpha]_D^{26} = -46.4°$ (c 0.53, MeOH)
IR(CHCl$_3$) 3290, 1650, 1506, 1230, 1019 cm$^{-1}$
$^1$H-NMR(CD$^3$OD): main peaks are δ: 0.67(d, 3H), 0.78(t, 3H), 1.30(t, 6H), 1.91(s, 3H), 4.1(m, 4H), 5.00(s, 4H), 6.84(d, 2H), 6.86(d, 2H), 7.09(d, 2H), 7.13(d, 2H), 7.3(bs, 10H)
Mass spectrum of the substance shows a molecular ion peak at m/Z 771.

The substance is thus identified as diethyl N-(N-acetyl-L-isoleucyl-O-benzyl-L-tyrosyl)-(−)-1-amino-2-(4-benzyloxyphenyl) ethylphosphonate.

REFERENCE EXAMPLE 4

In this example, 40 mg of the compound obtained in Reference Example 2, 26 mg of N-benzyloxycarbonyl-N-methyl-L-valine, and 11 mg of N-hydroxysuccinimide are dissolved in 1 ml of anhydrous ethylene glycol dimethyl ether, and the solution is stirred on a socium chloride-ice bath. Then, the solution is admixed with 22 mg of DCC and stirred for 3 hours. The mixture is then heated to room temperature and stirred for 26 hours. The formed N,N'-dicyclohexylurea is filtered off, and the filtrate is admixed with 50 ml of ethyl acetate. The organic layer is washed with an aqueous sodium bicarbonate solution, and then with water, and dried over anhydrous sodium sulfate. The solvent is distilled off under reduced pressure, and the residue is subjected to silica gel thin layer chromatography for fractionation recovery (chloroform:methanol=96:4), whereby 17 mg of the desired compound is obtained as a colorless glass-like substance having the following physical properties (yield: 27%).

$[\alpha]_D^{26} = -95.7°$ (c 0.68, MeOH)
IR(CHCl$_3$) 3410, 1674, 1509, 1222, 1040, 1020 cm$^{-1}$
$^1$H-NMR(CD$_3$OD): main peaks are δ: 0.76(d, 6H), 1.33(t, 6H), 2.52(bs, 3H), 4.12(m, 4H), 5.14(s, 2H), 6.66(d, 2H), 7.05(d, 2H), 7.10(s, 5H), 7.37(s, 5H)
Mass spectrum of the substance shows a molecular ion peak at m/Z 667.

The substance is thus identified as diethyl N-(N-benzyloxycarbonyl-N-methyl-L-valyl-L-phenylalanyl)-(−)-1-amino-2-(4-hydroxyphenyl) ethylphosphonate.

REFERENCE EXAMPLE 5

In this example, 15 mg of the compound obtained in Reference Example 3 is dissolved in 2 ml of methanol, admixed with 10 mg of 10% palladium-carbon, and subjected to catalytic reduction at room temperature for 3.5 hours. The catalyst is filtered off and the filtrate is subject to distillation under reduced pressure. The residue is dissolved in 50 ml of a mixed solvent of chloroform:methanol (9:1), and the solution is passed through a rather short column of silica gel column chromatography. The eluate is subjected to distillation under reduced pressure, and the residue is recrystallized from methanol, whereby 10 mg of the desired compound is obtained as colorless needle-like crystals having the following physical properties (yield: 86%).

Melting point: 292°–294° C. (dec)

$[\alpha]_D^{22} = -66.5°$ (c 0.10, MeOH)

IR(KBr): 3240, 1633, 1544, 1199, 1049, 1020 cm$^{-1}$ $^1$H-NMR(CD$_3$OD) main peaks are δ: 0.71(d, 3H), 0.82(t, 3H), 1.31(t, 6H), 1.94(s, 3H), 4.1(m, 4H), 6.64(d, 2H), 6.66(d, 2H), 7.00(d, 2H), 7.04(d, 2H)

Mass spectrum of the substance shows a molecular ion peak at m/Z 591.

The substance is thus identified as diethyl N-(N-acetyl-L-isoleucyl-L-tyrosyl)-(−)-1-amino-2-(4-hydroxyphenyl) ethylphosphonate.

REFERENCE EXAMPLE 6

In this example, 17 mg of the compound obtained in Reference Example 4 is dissolved in 1 ml of methanol-acetic acid (9:1), admixed with 10 mg of 10% palladium-carbon, and subjected to catalytic reduction for one day. The catalyst is filtered off, and the filtrate is subjected to distillaton under reduced pressure. The residue is subjected to silica gel thin layer chromatography for fractionation recovery (chloroform:methanol=9:1), whereby 6 mg of the desired compound is obtained as a colorless glass-like substance having the following physical properties (yield: 41%).

$[\alpha]_D^{26} = -40.9°$ (c 0.56, MeOH)

IR(CHCl$_3$) 3310, 1673, 1661, 1509, 1227, 1041, 1020, cm$^{-1}$ $^1$H-NMR (CD$_3$OD): main peaks are δ: 0.70(d, 3H), 0.76(d, 3H), 1.33(t, 6H), 1.93(s, 3H), 2.62(d, 1H), 4.13(m, 4H), 6.64(d, 2H), 7.04(d, 2H), 7.22(s, 5H)

Mass spectrum of the substance shows a molecular ion peak at m/Z 533.

The substance is thus identified as diethyl N-(N-methyl-L-valyl-L-phenylalanyl)-(−)-1-amino-2-(4-hydroxyphenyl) ethylphosphonate.

REFERENCE EXAMPLE 7

In this example, 2 mg of the compound obtained in Reference Example 5 is dissolved in 0.3 ml of 20% hydrobromic acid-acetic acid solution, and left standing at room temperature for 4 hours. The reaction solution is admixed with 5 ml of water, adjusted to pH 2 with aqueous 2N caustic soda, and passed through a column of HP-20 (nonionic porous resin made by Mitsubishi Kasei Kogyo Co.). After washing with water, the column is eluted with aqueous 0.1N ammoniacal 50% methanol, and the solvent is distilled off under reduced pressure, whereby 1 mg of the crude product is obtained. The crude product is then dissolved in a small amount of methanol, and the solution is subjected to high speed liquid chromatography (μBondapack C$_{18}$ (made by Waters Co.), 0.01M ammonium acetate (pH 5.0):acetonitrile=9:1, 4 ml/min.). The portions having a retention time of 2.7 minutes are collected, concentrated and freeze-dried, whereby the desired compound is obtained as a purified white solid. The physical properties of the thus obtained compound are as follows:

Melting point: 300° C. or higher $^1$H-NMR(D$_2$O, pD 4.5): main peaks are δ: 0.65(d, 3H), 0.81(t, 3H), 2.00(s, 3H), 3.99(d, 1H), 4.30(br, 1H), 4.65(dd, 1H), 6.83(d, 4H), 7.14(d, 2H), 7.20(d, 2H)

The substance is thus identified as N-(N-acetyl-L-isoleucyl-L-tyrosyl)-(−)-1-amino-2-(4-hydroxyphenyl) ethylphosphonic acid.

The hypotensive activity of the foregoing end product is determined in accordance with the following test procedure.

Test: measurement of hypotensive activity by observation of blood pressure:

The test was carried out according to the procedure set forth in "Evaluation of Pharmaceutical Effects (1), Pharmacological Test Procedure (II) (Basic Lectures on Development of Drugs V)" compiled by Kyosuke Tsuda, et al. and published by Chibun Shokan Publishing Co., on Oct. 10, 1971, pages 464–468.

As test animals, three spontaneously hypertensive rats (SHR) (male, body weight: 300–400 g) were used for each test group. The rats were anesthetized by intraperitoneal administration of 600 mg/kg of urethane and 60 mg/kg of α-chloralose. The trachea was maintained by a tracheotomy tube, and blood pressure was recorded on an ink oscillography through a pressure transducer (Nihon Koden MP-0.5) from a polyethylene cannula inserted into the left carotid artery. The test compound was dissolved in physiological saline solution to yield a dosage of 0.1 ml/100 g, and intravenously administered from a cannula inserted in the left femoral vein. The change in blood pressure was measured under anesthesia.

Changes in average blood pressure are shown in Table 1. Average blood pressure of 4 cases immediately before administration of the test compound was 143.5±21.3 mm Hg (average value+standard error).

TABLE 1

| Sample | Dosage (mg/kg, iv) | Before administration | Blood pressure change after administration (mm Hg) | | | |
|---|---|---|---|---|---|---|
| | | | 10 min. | 30 min. | 60 min. | 120 min. |
| test compound | 10 | 0 | −14 | −20 | −30 | +8 |
| test compound | 30 | 0 | −50 | −50 | −53 | −22 |

As is evident from the foregoing results, the test compound exhibits marked hypotensive activity.

REFERENCE EXAMPLE 8

In this example, 1 mg of the compound obtained in Reference Example 6 is dissolved in 0.3 ml of 20% hydrobromic acid-acetic acid solution, and the solution is left standing at room temperature for 4 hours. Thereafter, the procedure of Example 7 is followed whereby 0.5 mg of crude product is obtained. The crude product is dissolved in a small amount of aqueous 0.04N caustic soda, and the portion having a retention time of 1.8 minutes by high speed liquid chromatography (under the same conditions as in Example 7) are collected. After concentration and successive freeze-drying, the desired compound is obtained in purified form as a white solid having the following physical properties.

Melting point: 300° C. or higher $^1$H-NMR(D$_2$O, pD 11.9): main peaks are δ: 0.71(d, 3H), 0.79(d, 3H), 1.74(s, 3H), 2.69(d, 1H), 4.08(bt, 1H), 6.53(d, 2H), 7.01(d, 2H), 7.34(s, 5H)

The compound is thus identified as N-(N-methyl-L-valyl-L-phenylalanyl)-(−)-1-amino-2-(4-hydroxyphenyl) ethylphosphonic acid.

What is claimed is:

1. A compound of the formula:

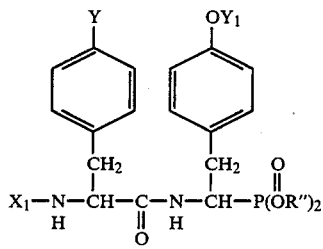

wherein
R'' is lower alkyl;
$X_1$ is benzyloxycarbonyl or t-butoxycarbonyl; and
Y is hydrogen, hydroxyl or a group represented by $OY_1$, wherein $Y_1$ is a hydroxyl-protecting group selected from the group consisting of methyl, ethyl, benzyl and benzyloxycarbonyl, and wherein the aromatic amino acid part has L-configuration and the 1-amino-2-(4-hydroxyphenyl)ethylphosphonic acid part has negative specific rotation.

2. A compound according to claim 1 wherein Y is hydrogen, hydroxyl or benzyloxy.

3. A compound according to claim 1 wherein $Y_1$ is benzyl.

4. A compound of the formula:

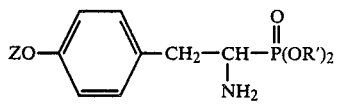

wherein R' is lower alkyl and Z is benzyl.

* * * * *

UNITED STATES PATENT AND TRADEMARK OFFICE
CERTIFICATE OF CORRECTION

PATENT NO. : 4,733,000
DATED : March 22, 1988
INVENTOR(S) : KUNIKATSU SHIRAHATA, ET AL.

It is certified that error appears in the above-identified patent and that said Letters Patent is hereby corrected as shown below:

Cover Page, at [54], In the Title, "OPTIALLY" should read --OPTICALLY--;

Cover Page, at [57], In the Abstract, "1-amino-2-(hydroxyphe-nyl)" should read --1-amino-2-(4-hydroxyphenyl)--;

Column 1, line 2, "OPTIALLY" should read --OPTICALLY--:

Column 5, line 22, "as the" should read --as above, in the--;

Column 8, line 23, "chlorideice" should read --chloride-ice--;

Column 12, line 21, "$^1$H-NMR(CD$^3$OD):" should read --$^1$H-NMR(CD$_3$OD):--;

Column 14, line 35, "(average value + standard error)." should read --(average value $\pm$ standard error).--.

Signed and Sealed this

Twelfth Day of July, 1988

*Attest:*

DONALD J. QUIGG

*Attesting Officer*     *Commissioner of Patents and Trademarks*